US006755868B2

(12) United States Patent
Rousseau (10) Patent No.: US 6,755,868 B2
(45) Date of Patent: *Jun. 29, 2004

(54) HERNIA REPAIR DEVICE (75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/104,305

(22) Filed: Mar. 22, 2002

(65) Prior Publication Data
US 2003/0181988 A1 Sep. 25, 2003

(51) Int. Cl.[7] .................................................. A61F 2/02
(52) U.S. Cl. ..................... 623/23.64; 606/151
(58) Field of Search ................. 623/23.64, 23.7–23.72, 623/23.75, 23.76; 600/37; 606/151

(56) References Cited

U.S. PATENT DOCUMENTS

| | | |
|---|---|---|
| 2,671,444 A | 3/1954 | Pease, Jr. |
| 3,054,406 A | 9/1962 | Usher |
| 3,874,388 A * | 4/1975 | King et al. ................. 606/232 |
| 4,347,847 A | 9/1982 | Usher |
| 4,452,245 A | 6/1984 | Usher |
| 4,561,434 A | 12/1985 | Taylor |
| 4,744,364 A | 5/1988 | Kensey |
| 4,769,038 A | 9/1988 | Bendavid et al. |
| 4,796,603 A | 1/1989 | Dahlke et al. |
| 4,852,568 A | 8/1989 | Kensey |
| 4,854,316 A | 8/1989 | Davis |
| 5,021,059 A | 6/1991 | Kensey et al. |
| 5,059,205 A | 10/1991 | El-Nounou et al. |
| 5,061,274 A | 10/1991 | Kensey |
| 5,108,420 A | 4/1992 | Marks |
| 5,108,430 A | 4/1992 | Ravo |
| 5,116,357 A | 5/1992 | Eberbach |
| 5,122,155 A | 6/1992 | Eberbach |
| 5,141,515 A | 8/1992 | Eberbach |
| 5,147,374 A | 9/1992 | Fernandez |
| 5,147,384 A | 9/1992 | La Rocca |
| 5,176,692 A | 1/1993 | Wilk et al. |
| 5,192,302 A | 3/1993 | Kensey et al. |
| 5,246,455 A | 9/1993 | Shikani |
| 5,254,133 A | 10/1993 | Seid |
| 5,258,000 A | 11/1993 | Gianturco |
| 5,290,217 A | 3/1994 | Campos |
| 5,304,187 A | 4/1994 | Green et al. |
| 5,316,543 A | 5/1994 | Eberbach |
| 5,334,217 A | 8/1994 | Das |
| 5,356,432 A * | 10/1994 | Rutkow et al. .......... 623/23.72 |
| 5,368,602 A | 11/1994 | de la Torre |
| 5,370,650 A | 12/1994 | Tovey et al. |
| 5,379,754 A | 1/1995 | Tovey et al. |
| 5,383,477 A | 1/1995 | DeMatteis |
| 5,397,331 A * | 3/1995 | Himpens et al. ............ 606/151 |
| 5,425,740 A | 6/1995 | Hutchinson, Jr. |
| 5,456,720 A | 10/1995 | Schultz et al. |
| 5,545,178 A | 8/1996 | Kensey et al. |
| 5,578,045 A | 11/1996 | Das |
| 5,593,441 A | 1/1997 | Lichtenstein et al. |

(List continued on next page.)

FOREIGN PATENT DOCUMENTS

| | | |
|---|---|---|
| EP | 0544485 | 6/1993 |
| EP | 0573273 | 12/1993 |
| EP | 0655222 | 5/1995 |

(List continued on next page.)

*Primary Examiner*—David H. Willse
*Assistant Examiner*—Suzette J. Jackson (57) ABSTRACT

An implantable prosthetic device adapted for use in repairing a hernia defect includes at least one body made from a biocompatible textile material. The body is provided with a first section and a second section inverted into the first section such that the second section is radially surrounded by the first section. The second section is movably connected to the first section such that the body is expandable or collapsible in a radial direction so as to conform to the size and shape of a hernia defect.

20 Claims, 5 Drawing Sheets

U.S. PATENT DOCUMENTS

| | | | |
|---|---|---|---|
| 5,634,931 A | | 6/1997 | Kugel |
| 5,634,944 A | | 6/1997 | Magram |
| 5,686,090 A | | 11/1997 | Schilder et al. |
| 5,716,408 A | | 2/1998 | Eldridge et al. |
| 5,741,297 A | | 4/1998 | Simon |
| 5,743,917 A | | 4/1998 | Saxon |
| 5,769,864 A | | 6/1998 | Kugel |
| 5,797,960 A | | 8/1998 | Stevens et al. |
| 5,824,082 A | | 10/1998 | Brown |
| 5,861,003 A | | 1/1999 | Latson et al. |
| 5,861,036 A | | 1/1999 | Godin |
| 5,916,225 A | | 6/1999 | Kugel |
| 5,944,738 A | * | 8/1999 | Amplatz et al. ............ 606/213 |
| 5,954,767 A | | 9/1999 | Pajotin et al. |
| D416,327 S | | 11/1999 | Kugel |
| 5,976,174 A | | 11/1999 | Ruiz |
| 6,066,777 A | | 5/2000 | Benchetrit |
| 6,113,623 A | | 9/2000 | Sgro |
| 6,113,641 A | | 9/2000 | Leroy et al. |
| 6,166,286 A | | 12/2000 | Trabucco |
| 6,174,322 B1 | | 1/2001 | Schneidt |
| 6,176,863 B1 | | 1/2001 | Kugel et al. |
| 6,180,848 B1 | * | 1/2001 | Flament et al. .......... 623/11.11 |
| 6,214,029 B1 | | 4/2001 | Thill et al. |
| 6,241,768 B1 | | 6/2001 | Agarwal et al. |
| 6,270,515 B1 | | 8/2001 | Linden et al. |
| 6,391,060 B1 | * | 5/2002 | Ory et al. ................ 623/23.76 |
| 6,425,924 B1 | * | 7/2002 | Rousseau ................ 623/23.64 |
| 2002/0133236 A1 | * | 9/2002 | Rousseau |
| 2003/0004579 A1 | * | 1/2003 | Rousseau et al. |

FOREIGN PATENT DOCUMENTS

| | | | |
|---|---|---|---|
| EP | 0888756 | | 1/1999 |
| EP | 0898944 A2 | | 3/1999 |
| EP | 1145693 A2 | | 10/2001 |
| FR | WO 01/85060 A1 * | 11/2001 | ............ A61F/2/00 |
| WO | 9213500 | | 8/1992 |
| WO | 9507666 | | 3/1995 |
| WO | 9530374 | | 11/1995 |
| WO | 9735533 | | 10/1997 |

* cited by examiner

HERNIA REPAIR DEVICE

FIELD OF THE INVENTION

The present invention relates to a hernia repair device and, more particularly, to a hernia repair device adapted to be implanted in a patient.

BACKGROUND OF THE INVENTION

Various prosthetic mesh devices have been proposed for use in repairing hernia defects (e.g., an opening in or the thinning of the tranversalis fascia through which the abdominal viscera can extrude). Some of these mesh devices are adapted for anterior-side hernia repair (i.e., repairing a hernia defect from an anterior side of the fascia proximate to the surgeon). For instance, a hernia defect can be repaired exclusively from the anterior side of the fascia by dissecting the sac from the surrounding structures, inverting the sac into an abdominal cavity and then closing the defect with the use of an overlay patch or with the use of a space-filling prosthesis having an overlay patch.

One type of prosthesis adapted for anterior-side hernia repair is made from a sheet of surgical mesh fabric folded into a multi-layered cone. In order to repair a hernia defect, the prosthesis is inserted into the defect to occlude the void. Because the prosthesis is stiff, it does not readily conform to the contour of the defect, forming gaps between the prosthesis and the interior wall of the defect and hence potentially causing recurrent herniation. The stiff, multi-layered prosthesis is also susceptible to kinking and buckling during its placement into the defect.

Additional examples of prostheses adapted for anterior-side hernia repair include the "PERFIX® Plug" and "MARLEX® Mesh Dart" devices marketed by C. R. Bard, Inc., Murray Hill, N.J. The "MARLEX® Mesh Dart" devices are implantable mesh prostheses which are hot-molded into a conical, non-compressible configuration and hence are not readily compliant to irregularities in muscle or tissue walls of hernia defects.

An implantable prosthesis similar to the "PERFIX® Plug" devices is disclosed in U.S. Pat. No. 5,356,432. More particularly, the implantable prosthesis is in the form of a conical plug made from a polypropylene mesh. Longitudinally extending pleats are hot-molded into the mesh to enhance the flexibility of the conical plug for the purpose of allowing the prosthesis to conform more readily to the contour of a herniated opening. Because of its conical shape, the prosthesis has a relatively large vertical length or profile. As a result, when the prosthesis is implanted into a hernia defect, its tip tends to press into and/or against a visceral sac, causing discomfort to the patient and/or impeding proper hernia repair. In one embodiment, the prosthesis is provided with filler layers incorporated into the interior of the prosthesis in order to minimize its contraction while the hernia defect is healed. These layers make the manufacturing of the prosthesis rather complicated.

Hernia defects can also be repaired from the posterior side of the fascia (i.e., the side of the fascia remote from the surgeon) by implanting prostheses in pre-peritoneal spaces to prevent peritonea from passing through the fascia defect. These prostheses are, in some instances, implanted with the use of laparoscopic techniques and, in other instances, require deployment from remote locations within the pre-peritoneal space. Examples of these prostheses are disclosed in U.S. Pat. Nos. 5,116,357, 5,254,133 and 5,916,225. The devices disclosed in these patents will be discussed in greater detail hereinbelow.

U.S. Pat. No. 5,116,357 discloses a hernia repair device having a plug positionable in an opening formed in the abdominal fascia, as well as a patch positionable over weakened portions of the abdominal fascia adjacent to the opening. A central extent of the patch is coupled to a proximal end of the plug. Resilient means is coupled to the patch and provided with memory to assume an extended shape for the proper positioning of the patch with respect to the weakened portions for the abdominal fascia. While this device provides a means of plugging and patching a circular defect, it does not conform to the shape of the naturally occurring defect. Additionally, it requires general anesthesia and additional instrumentation for its deployment at the site of a hernia defect with the use of a laparoscopic surgery.

U.S. Pat. No. 5,254,133 discloses a surgical implantation device for closing an enlarged, generally circular opening in a patient's body. The surgical implantation device includes a pair of generally planar portions interconnected by a connecting segment. While this device can reduce the amount of post-operative discomfort experienced by patients, it requires general anesthesia and additional instrumentation for its deployment at the site of a hernia defect with the use of a laparoscopic surgery.

U.S. Pat. No. 5,916,225 relates to a hernia mesh patch adapted for posterior-side hernia repair. More particularly, the patch includes a first layer sized and shaped so as to extend across and beyond a hernia defect. A second layer overlies the first layer to create a generally planar configuration for the patch. The first and second layers are joined together by a seam defining a periphery of a pouch formed between the first and second layers. An access slit is formed in one of the layers for insertion of a finger of a surgeon into the pouch to allow the surgeon to deform the planar configuration of the patch to facilitate insertion of the patch into the patient and to position the patch across the hernia. A resilient loop is located within the pouch for urging the patch to conform to the generally planar configuration across the hernia defect as the surgeon withdraws his or her finger. Due to the construction and deployment method of the patch, the surgeon needs to have proper dexterity in order to implant the patch at the site of a hernia defect. Moreover, while the resilient loop expands the device into a planar configuration, anatomical structures surrounding a hernia defect are typically non-planar. In such circumstances, the device may not readily conform to such anatomical structures.

Accordingly, there is a need for an implantable hernia repair device that has enhanced compliancy to the irregular shapes of hernia defects, that is simple to install without requiring general anesthesia and that has a reduced length or profile when implanted.

SUMMARY OF THE INVENTION

It is an object of the present invention to provide a prosthesis adapted for easy insertion into a hernia defect from an anterior-side thereof and capable of either expanding or collapsing radially so as to occlude and conform to the fascia wall of the hernia defect.

A further object of the present invention is to provide an implantable hernia repair device having a reduced length/profile when deployed in a hernia defect.

Yet another object of the present invention is to provide a prosthesis adapted for use in repairing hernia defects having varying sizes and shapes and adapted to be anchored to surrounding tissues such that it extends beyond the edge of a hernia defect on the anterior-side thereof to prevent migration.

The present invention overcomes the disadvantages and shortcomings of the prior art discussed above and achieves the aforementioned objects by providing a new and improved implantable prosthesis having at least one body made from a biocompatible textile material. The body is provided with a first section and a second section inverted into the first section such that the second section is radially surrounded by the first section. The second section is movably connected to the first section such that the body is expandable or collapsible in a radial direction so as to conform to the size and shape of a hernia defect. In one embodiment, a single, radially collapsible body is provided for use in repairing a hernia defect. In another embodiment, two identical bodies are connected to one another so as to form an implantable plug adapted to be radially expanded into position after its insertion into a hernia defect.

BRIEF DESCRIPTION OF THE DRAWINGS

For a more complete understanding of the present invention, reference is made to the following detailed description of exemplary embodiments considered in conjunction with the accompanying drawings, in which:

FIGS. 5–6b are schematic views illustrating the deployment of the hernia repair device shown in FIGS. 1 and 2 at the site of a hernia defect;

DETAILED DESCRIPTION OF THE EXEMPLARY EMBODIMENTS

Figure 1:
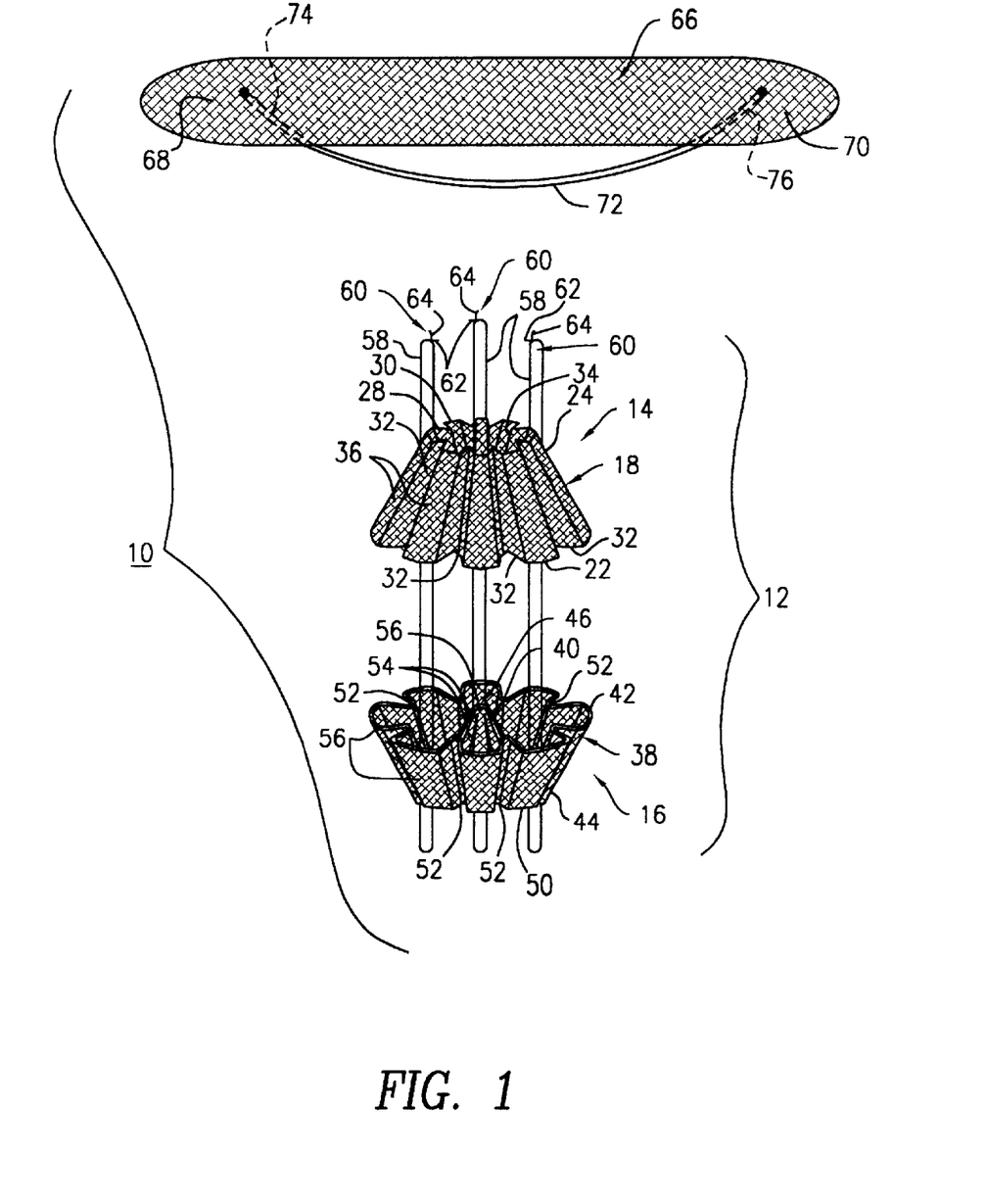
FIG. 1 is an exploded perspective view of a hernia repair device constructed in accordance with a first embodiment of the present invention.
Figure 2:
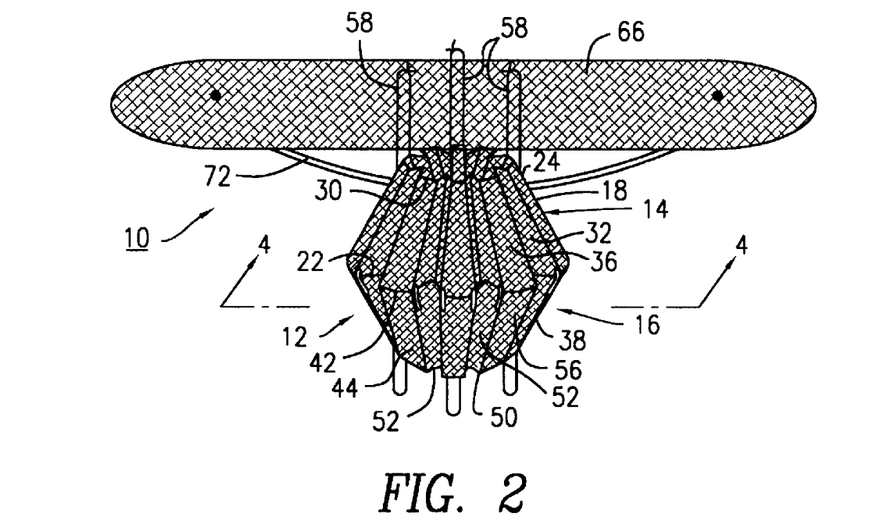
FIG. 2 is a perspective view of the hernia repair device shown in FIG. 1.

FIGS. 1 and 2 show a hernia repair device 10 constructed in accordance with a first embodiment of the present invention. The device 10 has a cone section 12 (also referred to hereinafter as "the plug") which includes a pair of cones 14, 16 attached to each other. Referring to FIGS. 1, 2, 3A and 4, the cone 14 is made from a single sheet of biocompatible medial textile, such as a polypropylene mesh, and hence has a unitary construction. The cone 14 is provided with a cross section having a "W" shape (i.e., the cone 14 is provided with an inverted construction). More particularly, the cone 14 includes an outer section 18 and an inner section 20 folded or inverted into the outer section 18 and hence radially surrounded by the outer section 18. The outer section 18 has a frusto-conical shape and includes an outer edge 22 and an inner end 24 remote from the outer edge 22. The outer edge 22 has a diameter which is greater than that of the inner end 24. The inner section 20 has a conical shape and is provided with an apex 26 (see FIGS. 3A and 4) and an open end 28 (see FIGS. 1 and 4) opposite the apex 26.

Figure 4:
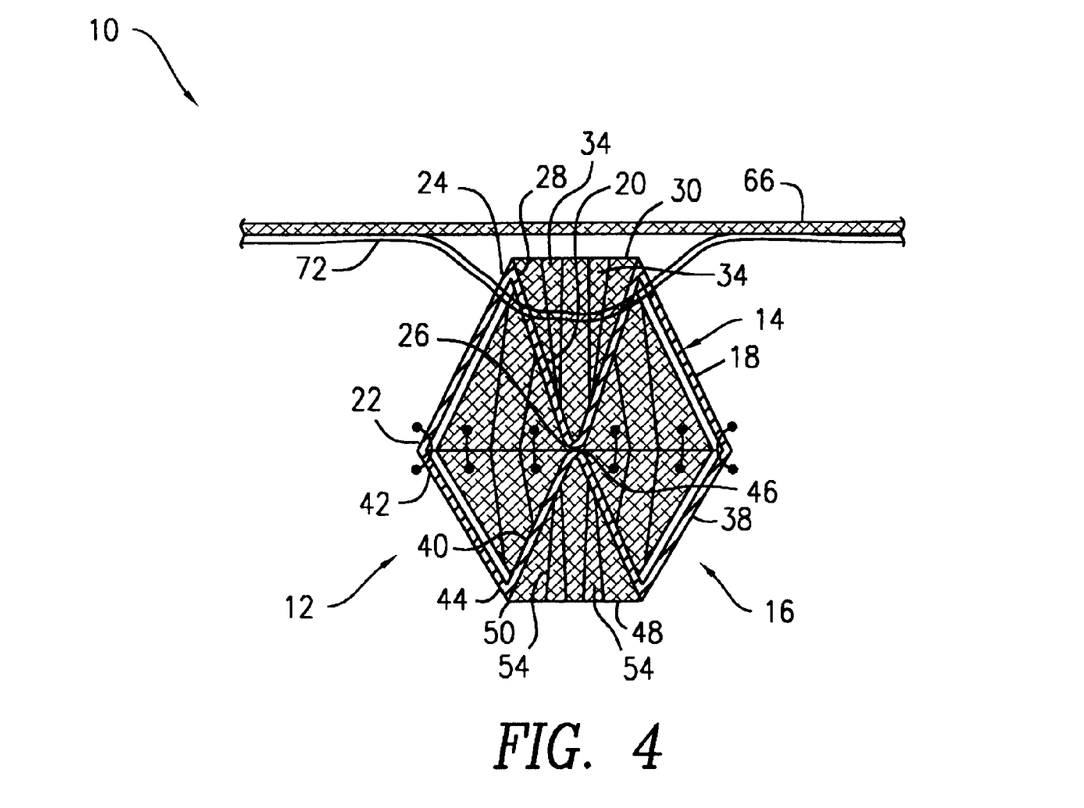
FIG. 4 is a cross-sectional view, taken along section lines 4—4 and looking in the direction of the arrows, of the hernia repair device shown in FIG. 2.

The open end 28 of the inner section 20 is connected integrally to the inner end 24 of the outer section 18 at a folding or pivot edge 30 (see FIGS. 1 and 4).

Figure 3A:
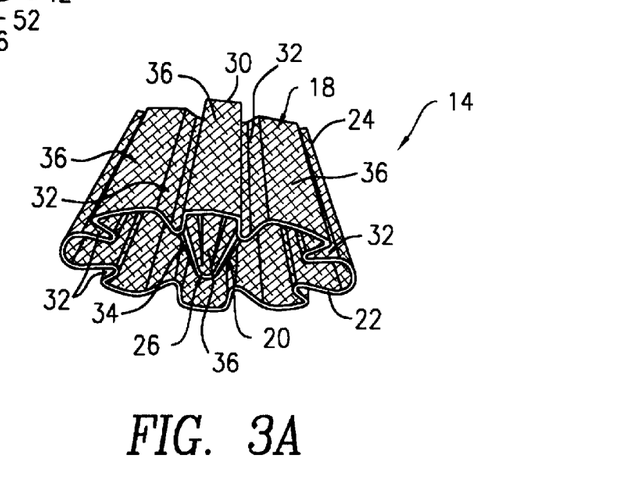
FIG. 3A is a perspective view of an inverted cone of the hernia repair device shown in FIGS. 1 and 2.
Figure 6A:
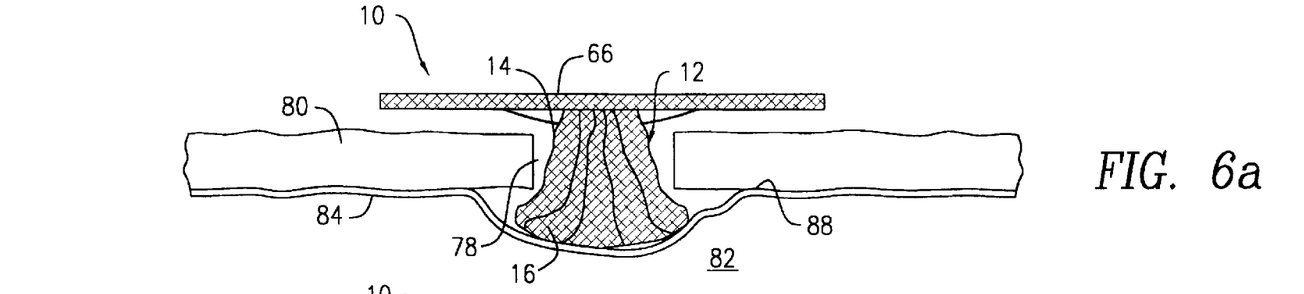
Figure 6B:
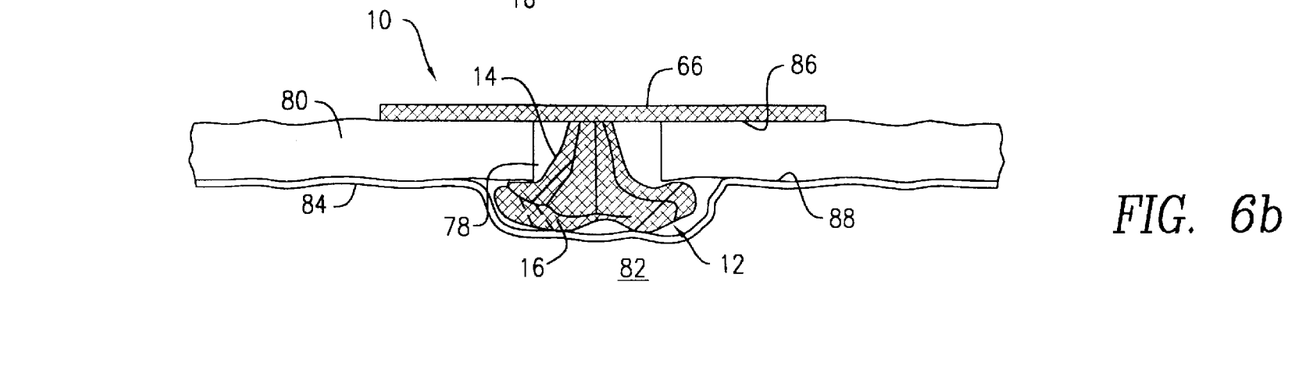

With reference to FIGS. 1, 2 and 3A, the outer and inner sections 18, 20 are provided with pleats 32, 34, respectively. The pleats 32, 34 are formed by a conventional thermoforming process. Alternatively, other conventional processes can be used. The pleats 32, 34 are formed such that a surface 36 is located between each adjacent pair of the pleats 32, 34. More particularly, each of the pleats 32, 34 projects radially inwardly from a corresponding pair of the surfaces 36. The pleats 32 also extend in a generally axial direction (i.e., in a direction generally parallel to the longitudinal axis of the plug 12) along the outer section 18 between the outer edge 22 and the inner end 24. Likewise, the pleats 34 extend in the generally axial direction along the inner section 20 between the open end 28 and the apex 26. Due to their pleated construction, the outer and inner sections 18, 20 are movable relative to one another. As a result, the cone 14 is radially expandable from a generally collapsed orientation (see FIG. 4) to an expanded orientation (see FIG. 6b) for purposes to be discussed hereinafter.

Now referring to FIGS. 1, 2, 3B and 4, the cone 16, which has a construction identical to that of the cone 14, is made from a single sheet of biocompatible medial textile, such as a polypropylene mesh, and hence has a unitary construction. The cone 16 is provided with a cross section having a "W" shape (i.e., the cone 16 has an inverted construction). More particularly, the cone 16 includes an outer section 38 and an inner section 40 folded or inverted into the outer section 38 and hence radially surrounded by the outer section 38. The outer section 38 has a frusto-conical shape and includes an outer edge 42 and an inner end 44 remote from the outer edge 42. The outer edge 42 has a diameter which is greater than that of the inner end 44. The inner section 40 has a conical shape and is provided with an apex 46 and an open end 48 (see FIGS. 3B and 4) opposite the apex 46. The open end 48 of the inner section 40 and the inner end 44 of the outer section 38 are integrally connected to one another at a folding or pivot edge 50 (see FIGS. 1, 3B and 4).

Figure 3B:
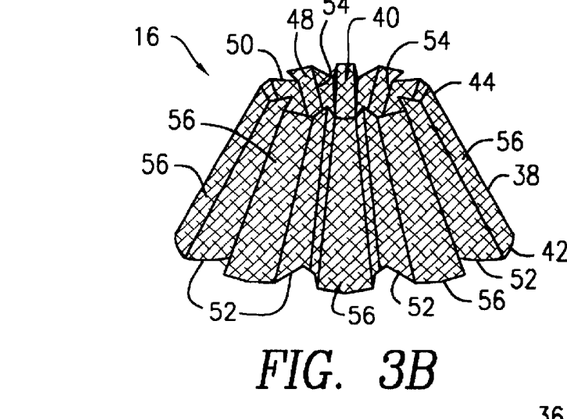
FIG. 3B is a perspective view of another inverted cone of the hernia repair device shown in FIGS. 1 and 2.

With reference to FIGS. 1, 2 and 3B, the outer and inner sections 38, 40 are provided with pleats 52, 54, respectively, formed by a conventional thermoforming process. Alternatively, other conventional processes can be used. The pleats 52, 54 are formed such that a surface 56 is located between each adjacent pair of the pleats 52, 54. More particularly, each of the pleats 52, 54 projects radially inwardly from a corresponding pair of the surfaces 56. The pleats 52 also extend in the generally axial direction (i.e., in the direction generally parallel to the longitudinal axis of the plug 12) along the outer section 38 between the outer edge 42 and the inner end 44. Likewise, the pleats 54 extend in the generally axial direction along the inner section 40 between the open end 48 and the apex 46. Due to their pleated construction, the outer and inner sections 38, 40 are movable relative to one another. As a result, the cone 16 is radially expandable from a generally collapsed orientation (see FIG. 4) to an expanded orientation (see FIG. 6b) for purposes to be discussed hereinafter.

Now referring to FIGS. 1, 2 and 4, the cones 14, 16 are secured to one another so as to form the conical section or plug 12. More particularly, the apex 26 of the cone 14 is attached to the apex 46 of the cone 16 by a conventional attaching method (e.g., bonding, stitching, welding, etc.). Similarly, the outer edges 22, 42 of the cones 14, 16, respectively, are matched and attached to each other by a conventional attaching method (e.g., bonding, stitching, welding, etc.). Because of the pleated construction of the cones 14, 16, the plug 12 is radially expandable from a collapsed orientation, in which the plug 12 is substantially erect (see FIG. 4), to an expanded orientation, in which the plug 12 is substantially flattened (see FIG. 6b).

With reference to FIGS. 1 and 2, the hernia repair device 10 may also be provided with suture loops 58 extending through the opposing cones 14, 16 for facilitating the axial compression of the opposing cones 14, 16 toward one another. More particularly, each of the suture loops 58 is formed by passing a suture through the cones 14, 16 and then forming a non-reversing slip knot 60, which has a trimmed dead tail 62 and a pull tail 64. For instance, one of the suture loop 58 extends through the apexes 26, 46 of the cones 14, 16, respectively, while the other suture loops 58 are located radially outwardly from the apexes 26, 46 (e.g., some of them extend through the folding edges 30, 50 of the cones 14, 16, respectively).

Still referring to FIGS. 1 and 2, the hernia repair device 10 is provided with a generally flat overlay patch 66 having opposing ends 68, 70. A fiber strand 72, which includes ends 74, 76, is attached to the overlay patch 66. More particularly, the end 74 of the strand 72 is attached to the end 68 of the overlay patch 66, while the end 76 of the strand 72 is attached to the end 70 of the overlay patch 66. The strand 72 also extends through the cone 14 so as to loosely attach the plug 12 to the overlay patch 66. Alternatively, the strand 72 can be passed through the center portion (i.e., the apexes 26, 46) of the opposing cones 14, 16. The strand 72 can also be passed through the hinge point (i.e., the edge 30) of the uppermost cone 14.

Figure 5:
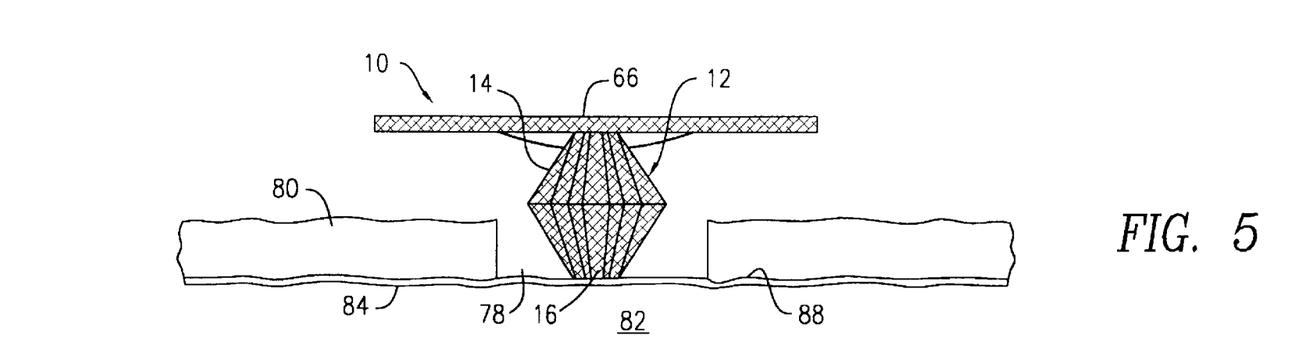

In order to repair a hernia defect 78 (see FIG. 5) formed in a fascia or abdominal wall 80, a hernia sac (not shown) is dissected and/or ligated, and then pressed back into the abdominal cavity 82 in a conventional manner. The expandable cone section 12 of the device 10 is then inserted into the defect 78, pressing against the peritoneum 84 (see FIG. 5). The contact with the peritoneum 84 causes the opposing cones 14, 16 to collapse axially, resulting in a radial expansion of the cone section 12 (see FIG. 6a). The plug 12 is inserted into the hernia defect 78 until the overlay patch 66 is substantially flush with an anterior side 86 of the fascia 80 (see FIG. 6b). With the overlay patch 66 held flush with the anterior side 86 of the fascia 80, the long portions (i.e., the pull tails) 64 of the suture loops 58 are pulled, causing the suture loops 58 to tighten. In response, the axially compressed cones 14, 16 are locked into the compressed condition, resulting in the permanent reduction of the axial length of the cone section 12. The axial compression of the cones 14, 16 causes the outer diameter of the cone section 12 to expand and the pleats 32, 34, 52, 54 to open up such that the cone section 12 assumes its expanded (i.e., substantially flattened) orientation (see FIG. 6b). When expanded, the cone section 12 partially fills and occludes the hernia defect 78, while conforming to the irregular shape or contour of the hernia defect 78. The overlay patch 66 can be sutured to the surrounding tissues using separate sutures and needles. The overlay patch 66 can also remain in place without fixation once the muscular layers are closed over the hernia defect 78.

It should be appreciated that the present invention provides numerous advantages over the prior art devices discussed above. For instance, the plug 12 is radially expandable without the use of any rigid or semi-rigid rings or members for expanding the plug 12. Due to the absence of such additional mechanisms, the plug 12 is readily compliant to anatomical structures of the hernia defect 78. In addition, when the plug 12 is in its expanded (i.e., generally flattened) orientation, it not only fills the hernia defect 78 but also occlude a posterior side 88 of the hernia defect 78 (see FIG. 6b). In this manner, the hernia repair device 10 inhibits the peritoneum 84 from extending into the hernia defect 78. Moreover, scar tissues growing into the flattened layers of the cones 14, 16 tend to further compress the plug 12 in the axial direction. As a result, the plug 12 cooperates with the overlay patch 66, which is positioned on the anterior side 86 of the hernia defect 78, so as to further secure the hernia repair device 10 from moving in an anterior or posterior direction. Further, in its expanded shape, the plug 12 has a small axial length or profile and does not therefore press deeply into and/or against a visceral sac.

It should be noted that the hernia repair device 10 can have numerous variations and modifications. For instance, the overlay patch 66 can be eliminated or replaced by other hernia repair mechanisms. In addition, the pleats 32, 34, 52, 54 can be provided with a different construction and/or shape. Each of the cones 14, 16 can also be made from separate parts (i.e., the cones 14, 16 can have a non-integral construction). Moreover, the hernia repair device 10 is adapted for use in repairing different types of hernia defects. The device 10 can also be constructed without the suture loops 58. In this configuration, the opposing cones 14, 16 are compressed axially during their insertion through the hernia defect 78, causing the radial expansion of the device 10 within the pre-peritoneal space.

Figure 7:
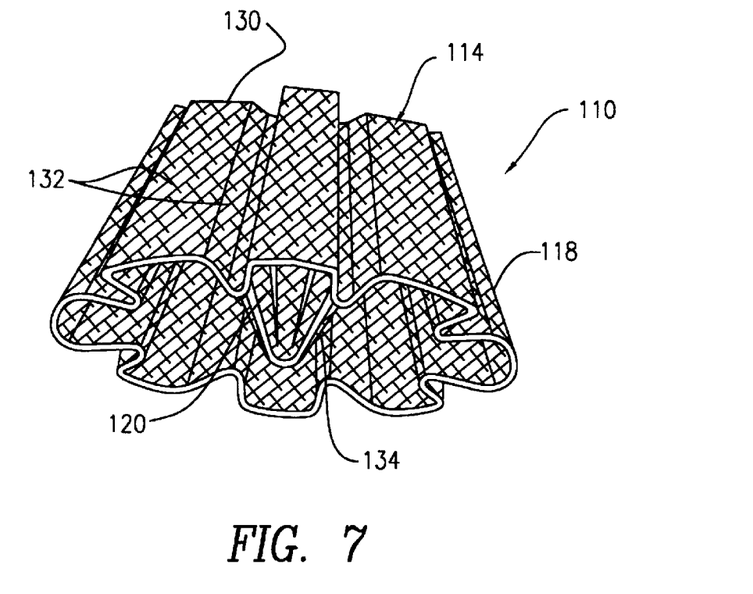
FIG. 7 is a perspective view of a hernia repair device constructed in accordance with a second embodiment of the present invention.
Figure 8:
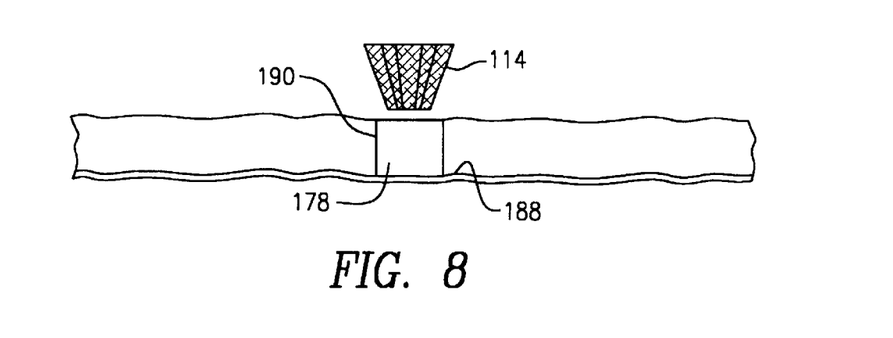
FIGS. 8 and 9 are schematic views illustrating the deployment of the hernia repair device shown in FIG. 7 at the site of a hernia defect.
Figure 9:
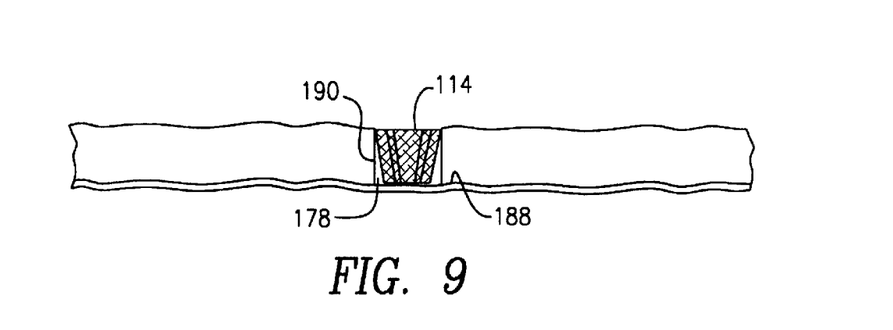

FIGS. 7–9 illustrate a hernia repair device constructed in accordance with a second embodiment of the present invention. Elements illustrated in FIGS. 7–9, which correspond, either identically or substantially, to the elements described above with respect to the embodiment of FIGS. 1–6b have been designated by corresponding reference numerals increased by one hundred. Unless otherwise stated, the embodiment of FIGS. 7–9 is constructed and assembled in the same basic manner as the embodiment of FIGS. 1–6b.

Referring to FIG. 7, a hernia repair device 110 includes a single cone 114 having a construction basically identical to that of the cone 14 or the cone 16 of the embodiment of FIGS. 1–6. For instance, the cone 114 includes outer and inner sections 118, 120 integrally connected to each other at a folding/hinged edge 130. The outer and inner sections 118, 120 are also provided with pleats 132, 134, respectively. In its normal orientation, the cone 114 has an outer diameter larger than the diameter of a hernia defect to be repaired.

In use, with the folding edge 130 facing a posterior side 188 of a hernia defect 178, the cone 114 is inserted into the defect 178. As the cone 114 is inserted into the defect 178 and engages a surrounding tissue wall 190 of same, it collapses in a radial direction so as to conform to the smaller size of the hernia defect 178 and to occlude the hernia defect 178. In this manner, a substantially stress-free repair of the hernia defect 178 can be performed.

It should be appreciated that the hernia repair device 110 also has numerous advantages over the prior art devices discussed above. For instance, because the inner section 120 is folded or inverted into the outer section 118, the hernia repair device 110 has a reduced vertical (i.e., axial) length or profile. Moreover, because the pleats 132, 134 are inverted radially inwardly, they provide multiple layers of mesh acting as filling materials for hernia defects.

It will be understood that the embodiments described herein are merely exemplary and that a person skilled in the art may make many variations and modifications without departing from the spirit and scope of the invention. All such variations and modifications, including those discussed above, are intended to be included within the scope of the invention as defined in the appended claims.

I claim:

1. An implantable prosthetic device adapted for use in repairing hernia defects, comprising at least one body made from a biocompatible textile material, said body having a first section and a second section, said second section being inverted into said first section such that said second section is radially surrounded by said first section, said second section being movably connected to said first section such that said body is expandable or collapsible in a radial direction so as to conform to the size and shape of a hernia defect.

2. The prosthetic device of claim 1, wherein said first section has a frusto-conical shape; and said second section has a conical shape.

3. The prosthetic device of claim 2, wherein said second section has an apex and an open end remote from said apex; and said first section has a first end, which is connected to said open end of said second section, and a second end remote from said first end.

4. The prosthetic device of claim 3, wherein said first section is integrally connected to said second section at an angle so as to form an edge between said first and second sections.

5. The prosthetic device of claim 4, wherein said first end of said first section has a first diameter; and said second end of said first section has a second diameter which is greater than said first diameter.

6. The prosthetic device of claim 5, wherein said first section includes a plurality of first pleats; and said second section includes a plurality of second pleats.

7. The prosthetic device of claim 6, wherein each of said first pleats extends between said first and second ends of said first section; and each of said second pleats extends between said open end and said apex of said second section.

8. The prosthetic device of claim 7, wherein each of said first pleats projects radially inwardly from said first section; and each of said second pleats projects radially inwardly from said second section.

9. The prosthetic device of claim 1, wherein said body is radially collapsible from a first shape, in which said body has a first outer diameter, to a second shape, in which said body has a second outer diameter smaller than said first outer diameter.

10. The prosthetic device of claim 1, further comprising another body made from a biocompatible textile material and connected to said body, said another body having a third section and a fourth section, said fourth section being inverted into said third section such that said fourth section is radially surrounded by said third section, said fourth section being movably connected to said third section such that said another body is radially expandable along with said body.

11. The prosthetic device of claim 10, wherein said body and said another body cooperate to form an implantable plug radially expandable from a collapsed shape to an expanded shape.

12. An implantable prosthetic device adapted for use in repairing a hernia defect, comprising a first body made from a biocompatible textile material, said first body having a first section and a second section, said second section being inverted into said first section such that said second section is radially surrounded by said first section; and a second body made from a biocompatible textile material, said second body having a third section and a fourth section, said fourth section being inverted into said third section such that said fourth section is radially surrounded by said third section, said first and second bodies are connected to one another so as to form an implantable body, said second and fourth sections being movably connected to said first and third sections, respectively, such that said implantable body is expandable in a radial direction from a collapsed shape to an expanded shape when said first and second bodies are urged to one another in an axial direction.

13. The prosthetic device of claim 12, said first section has a frusto-conical shape; said second section has a conical shape; said third section has a frusto-conical shape; and said fourth section has a conical shape.

14. The prosthetic device of claim 13, wherein said second section has a first apex and a first open end remote from said first apex; said first section has a second end, which is connected to said first open end of said second section, and a third end remote from said second end; said fourth section has a second apex and a fourth open end remote from said second apex, said first and second apexes being attached to one another; and said first section has a fifth end, which is connected to said fourth open end of said second section, and a sixth end remote from said fifth end, said sixth end and said third end being attached to one another.

15. The prosthetic device of claim 14, wherein said first section is integrally connected to said second section at an angle so as to form a first edge between said first and second sections; and said third section is integrally connected to said fourth section at an angle so as to form a second edge between said third and fourth sections.

16. The prosthetic device of claim 12, further comprising compressing means for axially compressing said first and second bodies to one another so as to cause said implantable body to expand radially.

17. The prosthetic device of claim 16, wherein said compressing means includes a plurality of suture loops extending through said first and second bodies.

18. The prosthetic device of claim 12, wherein said first section includes a plurality of first pleats projecting radially inwardly therefrom; said second section includes a plurality of second pleats projecting radially inwardly therefrom; said third section includes a plurality of third pleats projecting radially inwardly therefrom; and said fourth section includes a plurality of fourth pleats projecting radially inwardly therefrom.

19. An implantable prosthetic device adapted for use in repairing a hernia defect, comprising a body made from a biocompatible textile material, said body having a first section and a second section, said second section being inverted into said first section such that said second section is radially surrounded by said first section, said second section being movably connected to said first section such that said body is radially collapsible from a first shape to a second shape, said first section having a frusto-conical shape, and said second section having a conical shape.

20. The prosthetic device of claim 19, wherein said second section has an apex and an open end remote from said apex; and said first section has a first end, which is integrally connected to said open end of said second section, and a second end remote from said first end.

* * * * *